(12) United States Patent
Fang et al.

(10) Patent No.: US 11,221,475 B2
(45) Date of Patent: Jan. 11, 2022

(54) COVERSLIP FOR CELL CULTURE

(71) Applicant: GUANGZHOU JET BIO-FILTRATION CO., LTD., Guangdong (CN)

(72) Inventors: Xiangyuan Fang, Guangdong (CN); Huilun Li, Guangdong (CN); Yejames Yuan, Guangdong (CN); Jianhua Yuan, Guangdong (CN)

(73) Assignee: GUANGZHOU JET BIO-FILTRATION CO., LTD., Guangzhou (CN)

( * ) Notice: Subject to any disclaimer, the term of this patent is extended or adjusted under 35 U.S.C. 154(b) by 260 days.

(21) Appl. No.: 16/073,324

(22) PCT Filed: Dec. 15, 2016

(86) PCT No.: PCT/CN2016/110120
§ 371 (c)(1),
(2) Date: Jul. 26, 2018

(87) PCT Pub. No.: WO2018/107437
PCT Pub. Date: Jun. 21, 2018

(65) Prior Publication Data
US 2019/0041623 A1 Feb. 7, 2019

(51) Int. Cl.
*G02B 21/34* (2006.01)
*C12M 3/04* (2006.01)
(Continued)

(52) U.S. Cl.
CPC .............. *G02B 21/34* (2013.01); *C12M 3/04* (2013.01); *C12M 23/12* (2013.01); *C12M 23/38* (2013.01); *B01L 2200/141* (2013.01)

(58) Field of Classification Search
CPC ........... G02B 21/34; C12M 3/04; C12M 3/12; C12M 3/38; B01L 2200/141
(Continued)

(56) References Cited

U.S. PATENT DOCUMENTS 5,635,396 A * 6/1997 Fedun ................... B01L 9/52
435/283.1
5,858,770 A * 1/1999 Perlman ............... B01L 3/5085
435/297.5

FOREIGN PATENT DOCUMENTS

CN 201386105 Y * 1/2010
CN 201737950 U 2/2011
(Continued)

OTHER PUBLICATIONS

Nunc Catalog 2007-2008 (Jul. 15, 2016) (Year: 2016).*
(Continued)

*Primary Examiner* — Michael L Hobbs
*Assistant Examiner* — Lenora A Abel
(74) *Attorney, Agent, or Firm* — Yue (Robert) Xu; Apex Attorneys at Law, LLP

(57) ABSTRACT

A coverslip for cell culture, capable of achieving seamless adhesion between the coverslip for cell culture and a target culture device, so as to solve the technical problem that cell suspension flows into gaps between the coverslip and a culture dish. Moreover, the coverslip for cell culture has exquisite structure, and is easy to carry out batch experiment and comparison. The coverslip is flake-like with upper and lower surfaces being parallel to each other, and comprises: a coverslip substrate (1) and sub-coverslips (2); the coverslip substrate (1) is provided with at least N hollowed-out parts (11); the sub-coverslips (2) are fixedly connected in the
(Continued)

hollowed-out parts (11) by means of M fragile connecting pieces (3), wherein both N and M are natural numbers which are not related to each other.

7 Claims, 1 Drawing Sheet

(51) Int. Cl.
　　*C12M 1/32*　　(2006.01)
　　*C12M 1/00*　　(2006.01)
(58) Field of Classification Search
　　USPC .................................................. 435/288.3
　　See application file for complete search history.

(56) References Cited

FOREIGN PATENT DOCUMENTS

| CN | 202175681 U | | 3/2012 | |
| CN | 202631843 U | | 12/2012 | |
| CN | 204265761 U | * | 4/2015 | |
| CN | 204737964 U | | 11/2015 | |
| CN | 106754368 A | | 5/2017 | |
| EP | 0751215 A2 | | 1/1997 | |
| WO | 0151099 A1 | | 7/2001 | |
| WO | WO-0151099 A1 | * | 7/2001 | ............ C12M 23/48 |

OTHER PUBLICATIONS

Nunc Catalog Wayback Machine (Jul. 15, 2016)—Screenshot (Year: 2016).*
4titude Sealing Solutions 2017 Product Overview Catalog (Year: 2017).*
Machine English Translation Description of CN201386105Y (Year: 2010).*
Machine English Translation Description of CN204265761U (Year: 2015).*
International Search Report for PCT/CN2016/110120 dated Sep. 14, 2017, ISA/CN.

* cited by examiner

COVERSLIP FOR CELL CULTURE

This is a US National Phase application based upon PCT Application No. PCT/CN2016/110120, filed Dec. 15, 2016 and titled "COVERSLIP FOR CELLS".

FIELD

This invention relates to the field of cell culture technology, specifically to a coverslip for cells.

BACKGROUND

Coverslip is also called round coverslip for cells. Coverslip is an experimental material which provides solid phase surface for the growth of adherent cells so as to obtain in vitro cells according to the requirements of experiment and research. For example, coverslips or slides are immersed in cell culture medium so that the adherent cells grow on these substrates. The growth of adherent cells needs a support on which they can attach. The growth and proliferate of the cells on the support surface depends on adhesive factors secreted by the cells or provided in the culture medium. Coverslip is mainly used in the techniques such as cell morphology, immunocytochemistry, nucleic acid in situ hybridization and so on. At present, in many scientific research projects with large sample sizes and numerous indicators to be measured, there is an urgent need to prepare a large number of coverslips under the same experimental conditions and conduct various analyses and tests on them.

The coverslip is a round substrate with a thickness of 0.17 mm and a width of 8 mm, 14 mm, 20 mm, 25 mm and the like. The surface of the coverslip is TC (Tissue culture) treated so that both sides of which can be used (the front and the back are relative concepts). Surface of the coverslip is sterilized to ensure asepsis on the surface of the coverslip. Due to the permanent cation charges on surface of the coverslip, the cryostat tissue sections or cells are absorbed to the substrate by electrostatic interaction and covalent bond is formed between the substrate and the tissue section, so that the sections or cells can be tightly attached to the substrate without adhesive agent or protein coating. However, the coverslip is likely to move and overlap on the smooth bottom of cell culture dish so that the growth conditions and area of each coverslip with cell growth are different, leading to deviations of experimental results caused by poor identity of the coverslip. In order to solve the problems above, the manufacturers have made the following improvements to the cell culture device based on the design of the coverslip.

CN203569115U discloses a cell culture dish structure with coverslip, comprising: a culture dish and a coverslip, wherein the coverslip is embedded in a small hole of the culture dish, and a base set is provided at the bottom of the small hole with the same width, so that the coverslip is supported by the base. Therein, the main part of the coverslip is a round structure and a convex corner is provided at the outer edge of the coverslip, which is connected to the main part by a stiffener in the middle. When in using, the convex corner is above the base on one side.

CN202214367U discloses a coverslip holder for a culture dish with a high-density array, which includes a cross scaffold, and a plurality of projections are arranged at intervals on the cross scaffold in the horizontal direction of the same. The coverslips are fixed by the projections to effectively avoid floating, deflecting or moving.

By connecting the coverslip to the bottom of the culture dish with a stiffener, or fixing the coverslip between a groove at the bottom of the culture dish and the projections, both the two documents effectively solve the technical problems such as floating, deflecting or moving of the coverslip.

However, since the coverslips in both above documents are installed in a groove on the bottom surface of the culture dish, when cell suspension is dropped on the coverslip, the cell suspension easily flows into the gap between the culture dish and the coverslip along the edge of the coverslip due to the spatial position. Thus, the cells on the upper surface of the coverslip are not concentrated enough, and the result observation of the follow-up detection such as HE staining and immunocytochemical staining are affected. In addition, the coverslip disclosed in the above two documents have to be separately prepared and installed singly to a culture dish, which is a complicated process. Therefore, it is urgently needed to provide a coverslip structure that can achieve seamless connection of the coverslip and the target culture device, so as to solve the technical problem that cell suspension flows into the gap between the coverslip and the culture dish.

SUMMARY

In view of this, the present invention provides a coverslip for cells which realize seamless combination of coverslip and target culture device so as to solve the technical problem that cell suspension flows into the gap between the coverslip and the culture dish, and the structure is delicate, easy to be used in batch experiment and easy to be compared.

The present invention provides a coverslip for cells that is in a sheet shape and the upper and lower surfaces of which are parallel, said coverslip comprises:

a coverslip substrate 1 and a sub-coverslip 2;

wherein at least N hollow part 11 is provided on the coverslip substrate 1 and the sub-coverslip 2 is fixed to the hollow part 11 through M breakable connecting part 3, wherein N and M are natural numbers not related to each other.

Optionally, the sub-coverslip 2 comprises a sub-coverslip body 21 and a handle 22; and the sub-coverslip body 21 is connected with the handle 22 via a flexible part 23.

Optionally, a label concave area 24 or a label layer 25 for implicit order is provided on the handle 22.

Optionally, a colored layer is provided on the label concave area 24 or the label layer 25.

Optionally, the width of the breakable connecting part 3 is between 0.1 and 0.3 mm.

Optionally, the coverslip substrate 1, the sub-coverslip 2 and the breakable connecting part 3 are integrally formed.

Optionally, the sub-coverslip 2, the breakable connecting part 3 and the coverslip substrate 1 are all obtained by cutting an original coverslip substrate through numerical control process.

Optionally, the thicknesses of the coverslip substrate 1 and the sub-coverslip 2 are not less than 0.08 mm.

Optionally, a hydrophilic layer is provided on the surfaces of the coverslip substrate 1 and the sub-coverslip 2.

Optionally, the sub-coverslip 2 comprises a first sub-coverslip and a second sub-coverslip, and the sizes of the first sub-coverslip and the second sub-coverslip are different.

The key beneficial effects brought by improvement of the coverslip provided by the present invention are described hereinafter.

The coverslip is in a sheet shape and the upper and lower surfaces of which are parallel, comprising: a coverslip substrate 1 and a sub-coverslip 2; and there are hollow part 11 set on the coverslip substrate 1, and the sub-coverslip 2 is fixed to the hollow part 11 through M breakable connecting part 3. The coverslip of the present invention has an intact sheet structure. Each sub-coverslip 2 is fixed to the intact sheet with two tie points. There are at least N hollow part 11 on each coverslip substrate 1, which can be used by multiple cells at the same time, that is, they are suitable for batch experiment and are easy to be compared. If the coverslip needs to be installed in the target culture device, the intact sheet can be completely attached to the target culture device by physical and chemical methods, for example, the bottom surface of the inner wall of culture dish, culture flask or culture plate. In this way, there is no gap between each sub-coverslip 2 and the bottom surface of the inner wall of the culture device, which achieves seamless adhesion of the sheet to the target culture device, and thereby solving the technical problem that the cell suspension flows into the gap between the coverslip and the culture dish. Due to there is not any connection between the sub-coverslip used in the subsequent processing and the target culture device, the sub-coverslip can be easily detached from the breakable connecting part 3 as an object for further cell experiments.

BRIEF DESCRIPTION OF DRAWINGS

In order to describe the technical solutions in the examples of the present invention or the conventional art more clearly, the accompanying drawings used in description of the embodiments or the prior art will be illustrated briefly. It is obvious that the accompanying drawings in the following description are merely some examples of the present invention. For one of ordinary in the art, other drawings may also be obtained according to these drawings without any creative work.

In FIG. 2A, 24 represents a label concave area and in FIG. 2B, 25 represents a label layer.

DETAILED DESCRIPTION

The present invention provides a coverslip for cells which realize seamless connection of the coverslip and target culture device so as to solve the technical problem that cell suspension flows into the gap between the coverslip and the culture dish. The structure of the coverslip for cells is delicate, easy to be used in batch experiment and easy to be compared.

Figure 1:
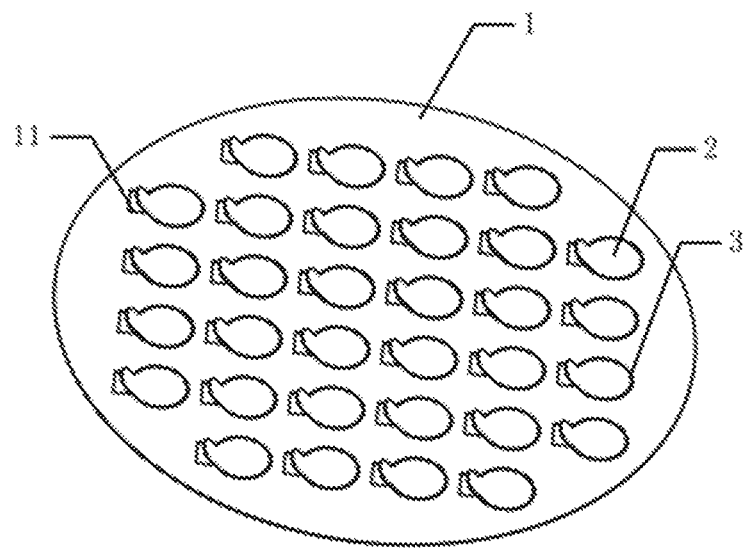
FIG. 1 is a structural diagram of a coverslip in one example of the present invention.
Figure 2:
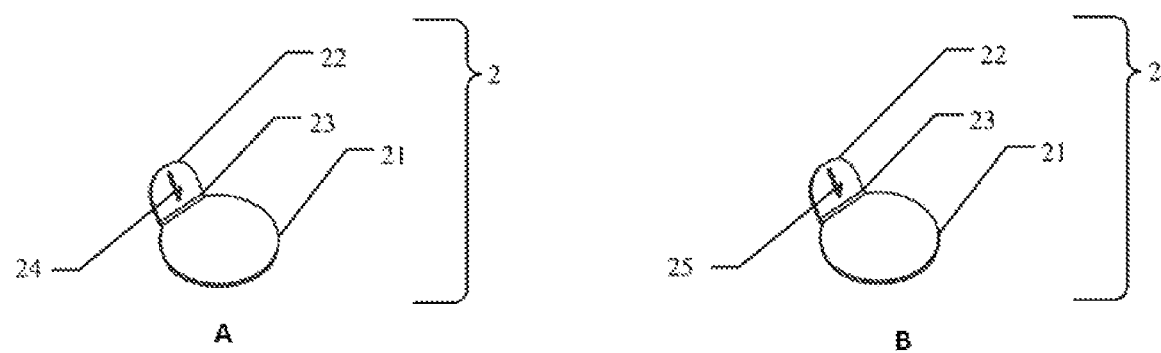
FIG. 2 is an enlargement of the sub-coverslip of FIG. 1.

Reference is made to FIGS. 1 to 2, the first example of the coverslip provided by the present invention specifically comprises:

a sheet shape coverslip, and the upper and lower surfaces of which are parallel;

a coverslip substrate 1 and a sub-coverslip 2;

at least N hollow part 11 is provided on the coverslip substrate 1 and the sub-coverslip 2 is fixed to the hollow part 11 through M breakable connecting part 3, wherein N and M are natural numbers not related to each other.

It should be noted that the coverslip substrate 1, sub-coverslip 2 and the breakable connecting part 3 are integrally formed;

the sub-coverslip 2, breakable connecting part 3 and the coverslip substrate 1 are obtained by cutting an original coverslip substrate through numerical control process. An example of laser cutting in practical application is described hereinafter.

Firstly, an original substrate was disposed in a laser beam cutting machine, for example, a rectangular substrate. When the laser beam cutting machine started working, the laser head emitted laser and the laser head was pulled by the robot arm. The laser head performed a first circular motion above the original substrate to obtain a first circular substrate.

Next, the laser head moved to the first circular substrate and performed a first circular arc motion at a predetermined position, leaving a first circular arc hollow groove on the first circular substrate, and the laser head stopped sending out laser.

Then, the laser head continuously moved a predetermined distance along the direction of the extension of the first circular arc and emitted laser again.

Then, the laser head performed a second circular arc motion continuously along the extension direction of the first circular arc.

Then, the laser head performed a first rectilinear motion along the longitudinal direction of the original substrate, after moving a predetermined distance and moving a predetermined distance along the vertical direction, the laser head performed a second rectilinear motion along the direction that is in the opposite direction and is parallel to the first rectilinear motion.

Then, a mirror motion of the second circular arc motion was carried out. In addition, a second circular arc hollow groove that was mirrored set to the first circular arc hollow groove was left. After the above laser engraving, a first group of coverslip that has a substrate 1, a sub-coverslip 2 and a breakable connecting part 3 were obtained.

In the present example, the coverslip specifically includes a coverslip substrate 1 and sub-coverslip 2. The coverslip substrate 1 is provided with hollow part 11, and the sub-coverslip 2 is fixed to the hollow part 11 with a breakable connecting part 3. The coverslip of the present invention has an intact sheet structure. Each sub-coverslip 2 is fixed to the intact sheet with two tie points. There is at least N hollow part 11 on each coverslip substrate 1 and they can be used by multiple cells at the same time, that is, they are suitable for batch experiment and are easy to be compared. If the coverslip needs to be installed in a target culture device, the intact sheet can be completely attached to the target culture device by physical and chemical methods, for example, the bottom surface of the inner wall of culture dish, culture flask or culture plate. In this way, there is no gap between each sub-coverslip 2 and the bottom surface of the inner wall of the culture device, which achieves seamless adhesion of the sheet to the target culture device, and thereby solving the technical problem that the cell suspension flows into the gap between the coverslip and the culture dish. Due to there is not any connection between the sub-coverslip used in the subsequent processing and the target culture device, the sub-coverslip can be easily detached via the breakable connecting part 3 as an object for further cell experiments.

The example of coverslip provided by the present invention will be further described hereinafter. The differences between the second example and the first example provided by the present invention are: the sub-coverslip 2 specifically comprises a sub-coverslip body 21 and a handle 22; the sub-coverslip 21 and the handle 22 are connected via a flexible part 23.

In the present example, since there are positive charges on the surface of the coverslip, touching by hand will neutralize the charges and lead to poor adhesive effects of the cells, so that affects subsequent operations. The handle 22 is connected through the flexible part 23. Normally, there is a certain inclination angle between the handle 22 and the body 21, which is a technical effect produced by the flexible part 23, so that it can be easily grasped by a device such as a tweezers.

The specific operation can be achieved by a laser beam cutting machine. In the first example, the technical solution of obtaining the sub-coverslip body 21 by laser cutting has been described.

Further, after forming the handle 22 by three times of rectilinear motions, the laser head is moved to the starting point of the joint between the handle 22 and the sub-coverslip body 21, and laser beam is emitted by half the power that is previously used to fuse the substrate, and then the laser head moved from starting point to the termination end of the joint. Whether a circular arc motion or a rectilinear motion is carried out is not specifically limited herein.

The example of coverslip provided by the present invention will be further described hereinafter. The differences between the third example and the above examples provided by the present invention are: the handle 22 is provided with a label concave area 24 or a label layer 25 for implicit order, the label concave area 24 or the label layer 25 is provided with a colored layer.

In the present disclosure, in order to facilitate sample matching in subsequent operations so as to trace the source of the sample, a nick may be left on the handle 22 by means of laser engraving, and the specific power of the laser engraving power can be consistent with that of the laser in the operation scheme of the second example.

It should be noted that the labels for implicit order include, but are not limited to, a group consisting of Arabic numerals, English letters, Roman numerals and Japanese kana, or a mixture thereof, which are not specifically limited herein.

It should be noted that the coverslip, culture device and cell suspensions are all in a transparent state, and it is not easy for the operator to distinguish the position where the slides are located, thereby affecting the operation of taking out the coverslip. Therefore, providing the colored layer in both the label concave area 24 or the label layer 25 effectively solves the technical problem. The specific coloring scheme is not described in detail here.

The example of coverslip provided by the present invention will be further described hereinafter. The difference between the fourth example and the above examples provided by the present invention is: the width of the breakable connecting part 3 is between 0.1 and 0.3 mm.

In the present example, when the width of the breakable connecting part 3 is less than 0.1 mm, the sub-coverslip 2 is easily folded. When the width is more than 0.3 mm, the breakable connecting part 3 is not easily broken by gripping the handle 22 with tweezers. In the present example, the limited range is verified by a mechanical test, and all the products in the range and all the products obtained by using the method are within the scope of protection of the present embodiment.

The example of coverslip provided by the present invention will be further described hereinafter. The difference between the fourth example and the above examples provided by the present invention is: the thickness of the coverslip substrate 1 and sub-coverslip is not less than 0.08 mm. At present, the thickness of the thinnest coverslip is 0.17 mm, while the thickness of the coverslip in the present example is 0.08 mm, which further increases the light transmittance, and effectively improves the quality assurance for subsequent experimental steps.

The example of coverslip provided by the present invention will be further described hereinafter. The difference between the fifth example and the above examples provided by the present invention is: the surfaces of the coverslip substrate 1 and the sub-coverslip 2 are provided with a hydrophilic layer.

It should be noted that a fixing layer is provided on the surface of the coverslip substrate 1 which connects to the bottom surface of the inner wall of the matching culture device. The other side of the fixing layer is used for the seamless connection with the bottom surface of the inner wall of the target culture device. The bottom surface of the inner wall of the target culture device is provided with a hydrophobic layer.

In the present example, the coverslip specifically includes a coverslip substrate and a sub-coverslip. There is a fixing layer provided on one surface of the coverslip substrate which connects to the bottom surface of the inner wall of the target culture device. The other side of the fixing layer is used for the seamless connection with the bottom surface of the inner wall of the target culture device, that is, the intact sheet is completely attached to the bottom surface of the inner wall of a target culture device such as a culture dish, a culture bottle or a culture plate by physical and chemical methods. In this way, there is no gap between each sub-coverslip and the bottom surface of the inner wall of the culture device, thereby effectively solving the technical problem that the cell suspension flows into the gap between the coverslip and the culture dish so that the cells grow on the back surface of the coverslip. Since there is no any connection between the sub-coverslip used for the subsequent treatment and the cell culture dish, the sub-coverslip can be easily detached via the breakable connecting part as an object for further cell experiments.

The coverslip has been described above. It should be further explained that the hydrophobic layer gives an apparent contact angle CA between 90 to 135 degrees, and even reaches a super-hydrophobic effect of 150 degrees or more.

It should be noted that the fixing layer is produced by physical or chemical treatment methods, and it can be obtained by three methods hereinafter.

The first method is UV curing. Generally, it refers to curing conditions or requirements of coatings, paints, inks, adhesives, glues, or other sealing sealants that require UV curing, which is distinguished from heat curing, adhesive curing, natural curing and the like.

The second method is ultrasonic curing. Ultrasound is generated by an ultrasonic generator. Since pressure and vibration are generated during the treatment of ultrasonic wave on the target material, mechanical stress is generated between the molecules of the material, and heat is relieved so that the material at the joint is softened to achieve adhesion.

The third alternative method is hot-pressing bonding, which is more easily to be applied than the previous two.

In the above examples, the shapes of the coverslip and the cell culture device are not limited. It is preferably a circle, but is not limited to a circle or a polygon, and may be triangle, rectangle, square, pentagon, hexagon and the like, which will not be listed herein. The laser cutting procedure also needs to be defined by the shape of the coverslip, and a plurality of sub-coverslips can be provided on one coverslip, and the size of each sub-coverslip may be different, so as to meet the requirements of different conditions.

The above description is only the specific examples of the present invention, but the protection scope of the present invention is not limited to this. Any of the ordinary skills in the art can easily think of changes or replacements within the technical scope disclosed of the present invention and should be covered by the scope of protection of the present invention. Therefore, the protection scope of the present utility should be subject to the protection scope of the claims.

The invention claimed is:

1. A coverslip for providing solid phase surface for the growth of adherent cells, which is a whole piece and in a sheet shape and upper and lower surfaces thereof are parallel, said coverslip comprises:
a coverslip substrate (1) and a sub-coverslip (2); wherein
at least N hollow part (11) is provided on the coverslip substrate (1) and the sub-coverslip (2) is fixed to the hollow part (11) through M breakable connecting part (3), wherein N and M are natural numbers not related to each other, and N is a number greater than 2;
the sub-coverslip (2) comprises a sub-coverslip body (21) and a handle (22); and the sub-coverslip body (21) is connected to the handle (22) via a flexible part (23); and the sub-coverslip body (21) and the coverslip substrate (1) are at the same level.

2. The coverslip according to claim 1, wherein a label concave area (24) or a label layer (25) for implicit order is provided on the handle (22).

3. The coverslip according to claim 2, wherein a colored layer is provided on the label concave area (24) or the label layer (25).

4. The coverslip according to claim 1, wherein the width of the breakable connecting part (3) is between 0.1 and 0.3 mm.

5. The coverslip according to claim 1, wherein the thicknesses of the coverslip substrate (1) and the sub-coverslip (2) are not less than 0.08 mm.

6. The coverslip according to claim 1, wherein a hydrophilic layer is provided on the surfaces of the coverslip substrate (1) and the sub-coverslip (2).

7. The coverslip according to claim 1, wherein the sub-coverslip (2) comprises a first sub-coverslip and a second sub-coverslip, and the sizes of the first sub-coverslip and the second sub-coverslip are different.

* * * * *